(12) United States Patent
Sajtos et al.

(10) Patent No.: US 7,169,950 B2
(45) Date of Patent: Jan. 30, 2007

(54) METHOD FOR PRODUCING MONOCARBONYL COMPOUNDS OR BISCARBONYL COMPOUNDS OR HYDROXYL COMPOUNDS

(75) Inventors: Alexander Sajtos, Leonding (AT); Engelbert Kloimstein, Eferding (AT); Curt Zimmermann, Riedmark (AT)

(73) Assignee: DSM Fine Chemicals Austria NFG GmbH & Co KG, Linz (AT)

( * ) Notice: Subject to any disclaimer, the term of this patent is extended or adjusted under 35 U.S.C. 154(b) by 551 days.

(21) Appl. No.: 10/469,306

(22) PCT Filed: Feb. 13, 2002

(86) PCT No.: PCT/EP02/01478

§ 371 (c)(1),
(2), (4) Date: Aug. 29, 2003

(87) PCT Pub. No.: WO02/072518

PCT Pub. Date: Sep. 19, 2002

(65) Prior Publication Data

US 2004/0073041 A1  Apr. 15, 2004

(30) Foreign Application Priority Data

Mar. 9, 2001  (AU) ............................. A370/2001

(51) Int. Cl.
*C07C 69/66* (2006.01)
*C07C 47/00* (2006.01)
*C07C 45/00* (2006.01)

(52) U.S. Cl. ............... 560/186; 568/442; 568/449; 568/451

(58) Field of Classification Search ......... 568/442, 568/449
See application file for complete search history.

(56) References Cited

U.S. PATENT DOCUMENTS 2,813,113 A * 11/1957 Goebel et al. ............... 562/524
4,242,309 A  12/1980 Carduck et al.
6,512,131 B1 * 1/2003 Best et al. ................... 554/133

FOREIGN PATENT DOCUMENTS

EP  1 095 700  5/2001
JP  05-140030  * 6/1993

OTHER PUBLICATIONS

Patent Abstracts of Japan, vol. 017, No. 513 (C-1111), Sep. 16, 1993 (abstract of JP 05-140030A, Jun. 8, 1993).

* cited by examiner

*Primary Examiner*—Paul A. Zucker
(74) *Attorney, Agent, or Firm*—Wenderoth, Lind & Ponack, L.L.P.

(57) ABSTRACT

The invention relates to a method for producing monocarbonyl compounds or biscarbonyl compounds or hydroxyl compounds by ozonizing, unsaturated organic carbon compounds that, per molecule, have one or more olefinic or aromatic double bonds, which can be cleaved by ozone, and by subsequently processing the ozonization products. According to the inventive method, unsaturated organic carbon compounds that, per molecule, have one or more olefinic or aromatic double bonds, which can be cleaved by ozone, are: (a) in 1 to 2 steps, continuously reacted with ozone in stoichiometric quantities or in excess while using counter educt currents and being in an organic solvent or in an aqueous solution inside a device, which consists of one to two absorption apparatuses, of devices for carrying away reaction heat, and of devices for separating the gas and liquid phases, and; (b) the peroxides resulting therefrom are, according to reaction parameters from step (a), converted into the corresponding monocarbonyl compounds or biscarbonyl compounds or hydroxyl compounds either by continuous or discontinuous hydrogenation, oxidation or heating.

16 Claims, No Drawings

METHOD FOR PRODUCING MONOCARBONYL COMPOUNDS OR BISCARBONYL COMPOUNDS OR HYDROXYL COMPOUNDS

The invention relates to a process for the preparation of monocarbonyl or biscarbonyl or hydroxyl compounds from unsaturated organic carbon compounds having one or more olefinic or aromatic double bonds in the molecule.

The ozonolysis of olefins gives, in an environmentally friendly manner, carbonyl compounds, such as aldehydes or ketones, or, depending on the work-up conditions, their hemiacetals, acetals or ketals, and also hydroxyl compounds which represent valuable starting materials in preparative organic chemistry.

The preparation of carbonyl or hydroxyl compounds from organic compounds which have, as structural element, one or more C=C double bonds in the molecule by means of a two-stage ozonolysis and reduction process is known. In carrying out this method, the first stage in most cases uses an excess of ozone in order to achieve as complete as possible ozonization of the double bond. The reductive cleavage, which takes place in the second stage, presents problems again and again since the peroxide-containing ozonization products are unstable and, in the absence of metallic hydrogenation catalysts, undergo rearrangements or decomposition particularly readily before they can be reduced to the corresponding carbonyl compounds. Furthermore, in the case of noble metal catalysts and prolonged contact with peroxide-containing solutions, losses in activity of the catalyst have been observed, meaning that the solutions do not usually become entirely peroxide-free upon reductive cleavage by hydrogenation and, in addition to the difficulties with isolation of the end-products, losses in yield and a risk of explosion also have to be accepted. To avoid these difficulties, U.S. Pat. No. 3,145,232 recommends a process for the preparation of carbonyl compounds in which the reductive cleavage is carried out after the ozonolysis at temperatures below $-40°$ C. in the presence of a trialkyl phosphite. As well as the high expenditure on apparatus for producing the extremely low reaction temperatures, such a reaction procedure requires the use of absolutely anhydrous solvents since the trialkyl phosphites are hydrolyzed extremely rapidly in hydrous solvents.

Furthermore, separation of the free carbonyl compounds from the phosphate esters which form during the reduction presents considerable difficulties.

Since it has been demonstrated that low reaction temperatures have a disadvantageous effect on the activity of the reducing agent used, resulting in losses in yield, according to a process for the preparation of aliphatic, aromatic and heteroaromatic aldehydes as is described in U.S. Pat. No. 3,637,721, although the ozonolysis of the C=C double bond is carried out at $-50°$ C., while the reaction temperatures during the course of the reductive cleavage of the ozonization products with aromatic or aliphatic disulfides is increased to $50°$ C. However, in said process, separation of the sulfoxides which form as secondary products during the reduction, for example dimethyl sulfoxide, from the aldehydes which form as process products has turned out to be extremely difficult and cannot be carried out at all in many cases without derivatization of the aldehydes.

Finally, U.S. Pat. No. 3,705,922 or DE-A-2 514 001 describe the preparation of carbonyl compounds by means of an ozonolysis and reduction process in which the unsaturated compounds serving as starting material are reacted with an excess of ozone, and the ozonization products formed in the process are reductively cleaved by catalytic hydrogenation. However, in the process, excess ozone must again be removed prior to the reductive cleavage to protect the hydrogenation catalyst against losses in activity by flushing the reaction solution with an inert gas, for example with nitrogen, in a suitable processing operation.

To carry out the hydrogenation, the catalyst, which is preferably a noble metal catalyst, is, then, added directly to the reaction mixture formed during the ozonolysis, and hydrogen is introduced to saturation.

Since noble metal catalysts are deactivated upon prolonged contact with organic peroxides, in the known processes the yield during the hydrogenation depends on the amount of hydrogenation catalyst used in each case. As is clear from a comparison of the examples in U.S. Pat. No. 3,705,922, the yield decreases by about 10% despite a correspondingly extended reaction time if, for the same size batch, only 0.2 g of a $Pd/Al_2O_3$ catalyst are used in place of 0.5 g. However, said publications give no details on the possibilities of regeneration or reuse of the noble metal catalysts used when the hydrogenation is complete either.

Processes for the preparation of carbonyl compounds, their hemiacetals, acetals or ketals by ozonolysis and reduction which aim to avoid the above disadvantages and which are carried out on an industrial scale are described in EP-B-0 146 784 or EP-B-0 147 593. According to the disclosure of these two patent specifications, compounds which have olefinic double bonds are reacted in a lower aliphatic alcohol at temperatures of from $-80°$ C. to $20°$ C. with the equivalent amount of ozone, and then the peroxidic reaction solution is fed into a suspension of a hydrogenation catalyst with the addition of hydrogen in a manner such that the peroxide concentration in the reaction mixture does not exceed 0.1 mol/l. Since this type of reaction procedure produces acidic secondary products which would poison and rapidly deactivate the catalyst, the pH of the reaction mixture has to be controlled by adding a base.

In the process variants known hitherto, both the ozonolysis step and also the hydrogenation are carried out batchwise. The excess of ozone which is used in most cases also has a negative effect in the case of these processes since, for example, it has to be blown out using inert gas prior to the hydrogenation step.

DE 27 13 863 describes a continuous ozonolysis, in particular of long-chain or higher molecular weight compounds, such as olefins, oleic acid or linoleic acid, in the presence of water. The water is used here in place of an external cooling cycle and thus serves for the in situ dissipation of the heat of the reaction. This process is only for rapidly reacting substrates, such as oleic acid and only for aqueous systems, not for purely organic systems which, however, are used for the greater part in the ozonolysis.

Surprisingly it has now been found that the disadvantages associated with the known processes can be avoided according to the present invention by a simple and economic process in which, in a continuous procedure, an unsaturated organic carbon compound having one or more olefinic or aromatic double bonds is reacted, despite known disadvantages, with an excess of ozone, and then the peroxide-containing ozonization products, likewise in a continuous procedure in dilute solution at a low concentration of peroxides, are rapidly reductively cleaved or converted into the desired end products by means of oxidation or simple heating.

In comparison with the known processes, the process according to the present invention gives carbonyl or hydroxyl compounds in a comparable yield and purity by the continuous processing method in a more simple and more economic way, with the constant and easy-to-control parameters, the reduced requirement for monitoring and the lower peroxide content in the plant having proven particularly advantageous. In the process according to the invention, the catalysts are preserved and in no way chemically poisoned during a prolonged period of operation, meaning that, firstly, they remain stable for years and, secondly, do not exhibit noticeable loss in activity even without regeneration and work-up upon reuse. All of these advantagous properties could not have been expected in view of the prior art.

Accordingly, the present invention provides a process for the preparation of monocarbonyl or biscarbonyl or hydroxyl compounds by ozonization of unsaturated organic carbon compounds which have one or more olefinic or aromatic double bonds which can be cleaved by ozone in the molecule, and subsequent work-up of the ozonization products, which comprises reacting unsaturated organic carbon compounds which have one or more olefinic or aromatic double bonds which can be cleaved by ozone in the molecule, a) in an organic solvent or in aqueous solution in 1 to 2 steps continuously in equipment consisting of one to two absorption apparatuses, devices for dissipating heat of the reaction and devices for separating the gas and liquid phase, with countercurrent reactant streams, with ozone in stoichiometric amounts or in excess and b) converting the peroxides which form into the corresponding monocarbonyl or biscarbonyl or hydroxyl compounds either by continuous or discontinuous hydrogenation, oxidation or heating, depending on the reaction parameters from step a).

The process according to the invention can be used to prepare a large number of very different monocarbonyl or biscarbonyl or hydroxyl compounds.

Examples thereof are monocarbonyl or biscarbonyl or hydroxyl compounds of the formula I

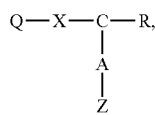

in which
Z is either OH or O and A, when Z is OH, is a single bond and, when Z is O, is a double bond
Q is hydrogen or the radicals

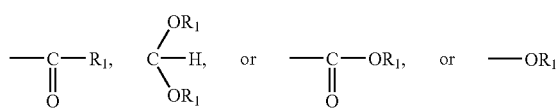

where $R_1$ is H or an ester moiety derived from chiral or nonchiral primary, secondary or tertiary alcohols,
X is a straight-chain or branched mono- or divalant, aliphatic alkyl or alkylene radical having 1 to 50 carbon atoms, where this alkyl or alkylene radical may be substituted by one or more groups which are inert under the reaction conditions; an optionally substituted, straight-chain or branched aliphatic alkyl or alkenyl radical having 2 to 50 carbon atoms, where one or more of the —$CH_2$ groups of the alkyl or alkylene chain is replaced by an oxygen atom, a nitrogen atom, a sulfur atom or an —$SO_2$ group; a radical of the formula —$(CH_2)_m$—O—CO—$(CH_2)_p$, where m may be an integer from 1 to 4 and p may be an integer from 1 to 6; a phenyl or phenylene radical, where this phenyl or phenylene radical may be substituted by one or more groups which are inert under the reaction conditions; a mono- or divalent alkylarylene or alkylenearylene radical having 7 to 50 carbon atoms, where these radicals may be substituted by one or more groups which are inert under the reaction conditions; an optionally substituted heterocycle with one or two heteroatoms in the ring or a single bond between two adjacent carbon atoms, and R is hydrogen, a $C_1$ to $C_{20}$-alkyl radical, —$OR_1$ or the radical

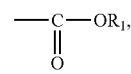

or X and R together form a mono- or bicyclic radical having 4 to 20 carbon atoms which may be mono- or polysubstituted by groups which are inert under the reaction conditions, are prepared.

Ester moiety derived from chiral or nonchiral alcohols is to be understood as meaning esters of primary, secondary or tertiary alcohols. Esters of primary alcohols are preferably derived from methanol, ethanol, butanol, propanol or hexanol. Esters of secondary or tertiary alcohols are preferably derived from acyclic, monocyclic, bicyclic, terpene alcohols, from acyclic, monocyclic, tricyclic, sesquiterpene alcohols, di- or triterpene alcohols which may be optionally substituted.

Examples of suitable substituents which are inert under the reaction conditions are:

$C_1$–$C_{20}$-alkyl or alkoxy or alkylalkoxy groups, such as, for example, methyl, ethyl, isopropyl, butyl, hexyl, octyl decyl, dodecyl, methoxy, ethoxy, butoxy, hexoxy, methoxymethyl, methoxyethyl, ethoxymetyl, ethoxyethyl, etc.;

nitro, halogen, hydroxyl, CN, $CONH_2$, carboxyl, carboxylate, amino, $SO_3H$ groups, etc. Compounds which can be prepared are, for example, benzaldehyde, 4-methylbenzaldehyde, 3,4-methylendioxybenzaldehyde, p-nitrobenzaldehyde, p-tolualdehyde, pyridine-4-aldehyde, pyridine-2-aldehyde, nonanal, acetoxyacetaldehyde, methyl or ethyl pyruvate, ethyl α-ketobutyrate, diethyl mesoxalate, 3,3-dimethoxypropanal, 3,3-di-n-butoxypropanal, succindialdehyde, adipaldehyde, 1,8-octanedial, 3-thiaglutaraldehyde 3,3-dioxide, homophthalaldehyde, dimethyl 1,6-hexanedial-3,4-dicarboxylate, o-phthalaldehyde, 3-oxaglutaraldehyde, methyl glyoxylate methanol hemiacetal, n-butyl glyoxylate methanol hemiacetal, n-ocyl glyoxalate methanol hemiacetal, menthyl glyoxylate, borneyl glyoxylate, fenchyl glyoxylate, 8-phenylmenthyl glyoxylate, 2-sulfobenzoic acid, 4-nitro-2-sulfobenzoic acid, 4-nitro-2-sulfobenzaldehyde, 4-aminobenzoic acid, therephthalic acid, 2,3-pyridinedicarboxylic acids which are unsubstituted or substituted in position 4 and/or 5 and/or 6 by $C_1$–$C_4$-alkyl or alkoxy, $C_1$–$C_4$-alkyl-$C_1$–$C_4$-alkoxy, halogen hydroxyl or nitro, 2-acetylnicotinic acid, nopinone, hydroxymethylpyridines, methyl lactate, butyroxyacetaldehyde etc.

Suitable starting compounds for the ozonization are unsaturated, organic carbon compounds having one or more olefinic or aromatic double bonds which can be cleaved off by ozone in the molecule.

These are, for example, unsaturated compound of the general formula II

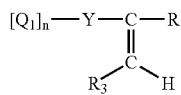

in which n is 0 or 1, $Q_1$ is hydrogen or the radicals

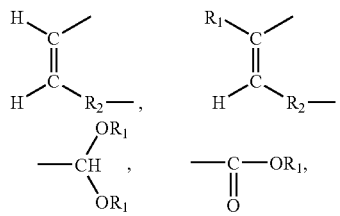

where $R_1$ is as defined above,
$R_2$ and $R_3$, independently of one another, are hydrogen, a $C_1$ to $C_4$-alkyl radical, a phenyl or pyridyl radical which is unsubstituted or substituted by groups which are inert under the reaction conditions, or are a —$COOR_1$ radical, or are a radical of the formula $(CH_2)_m$—O—CO—$(CH_2)_p$, where m may be an integer from 1 to 4 and p may be an integer from 1 to 6,
or, if n is 1 and $Q_1$ is the radical

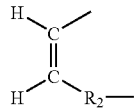

$R_2$ and $R_3$ are together a single bond between two adjacent carbon atoms or are an alkylene radical having 2 to 4 carbon atoms if Y is an o-phenylene radical or an alkylene radical having 2 to 4 carbon atoms and R is a hydrogen atom, otherwise Y has the same meaning as X in formula I, if n is 1, or if n is 0, is either hydrogen or, together with $R_3$ or with $R_3$ and the C═C double bond, is an optionally substituted, aliphatic, araliphatic, aromatic or heteroaromatic radical having 1 to 50 carbon atoms which may be interrupted by oxygen, nitrogen or sulfur, or Y with $R_3$ and the C═C double bond is an optionally substituted mono- or bicyclic radical having 4 to 20 carbon atoms which can contain 1 or 2 heteroatoms from the group S, N or O, or Y and R together form a mono- or bicyclic radical having 4 to 20 carbon atoms which can be mono- or polysubstituted by groups which are inert under the reaction conditions and R is as defined in formula I.

Suitable substituents are again $C_1$–$C_{20}$-alkyl or alkoxy or alkylalkoxy groups, such as, for example, methyl, ethyl, isopropyl, butyl, hexyl, octyl, decyl, dodecyl, methoxy, ethoxy, butoxy, hexoxy methoxymethyl, methoxyethyl, ethoxymetyl, ethoxyethyl, etc.;
nitro, halogen, hydroxyl, CN, $CONH_2$, carboxyl, carboxylate, amino, $SO_3H$ groups, etc.

As starting materials, it is accordingly possible to react those compounds of the formula II to give the corresponding monocarbonyl or biscarbonyl or hydroxyl compounds of the formula I in which, for example, Y is to be understood as meaning an aliphatic radical, for example a divalent, straight-chain or branched alkylene radical having 1 to 50, preferably 1 to 20, carbon atoms, where a $CH_2$ radical in the aliphatic chain may be replaced by oxygen, nitrogen, sulfur or by the $SO_2$ radical. Examples of an araliphatic radical are aralkylene, alkylarylene or alkylene-arylene radicals having, for example, 7–50, preferably 7–20, carbon atoms. An example of an aromatic radical is, for example, a phenylene radical and an example of a heteroaromatic radical is a divalent radical of a, for example, mono- or bicyclic heterocycle having one or two heteroatoms in the ring, where the rings are preferably five- or six-membered. The above-mentioned radicals can also be substituted by one or more groups which are inert under the reaction conditions, for example by alkyl, alkoxy or alkoxycarbonyl groups having in each case 1 to 10 carbon atoms, preferably having 1 to 4 carbon atoms, or by nitro groups.

In a preferred manner, unsaturated compounds of the formula IIa

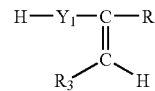

in which
R is defined as in formula I and $R_3$ is defined as in formula II and
$Y_1$ and $R_3$ are identical and are both the radical —$(CH_2)_m$—O—CO—$(CH_2)_p$ where m is 1 or 2 and p is 1, 2 or 3, or
$Y_1$ together with hydrogen, is a phenyl radical optionally substituted in the ortho and/or meta and/or para position or an optionally substituted five- or six-membered heteroaryl radical with a heteroatom in the ring, but particularly preferably the para-nitrophenyl, p-tolyl, 2- or 4-pyridinyl radical or, together with the C═C double bond, is an optionally substituted mono- or bicyclic heterocycle, such as, for example, unsubstituted or substituted quinoline or indole, or in which $Y_1$ and R together form a bicyclic radical having 4 to 10 carbon atoms which may be mono- or polysubstituted by groups which are inert under the reaction conditions, are reacted to give the correspondingly preferred carbonyl or hydroxyl compounds.

Examples of unsaturated compounds of the formula IIa are butenediol(1,4) dibutyrate, para-nitro- or para-methylstyrene, 2- or 4-vinylpyridine, quinoline, 8-methylquinoline, 3-ethyl-8-methylquinoline, indole, thiophene dioxide, stilbene-2,2'-disulfonic acid, 4,4'-dinitrostilbene-2,2'disulfonic acid, 4,4'-vinylienedianiline, 4,4'-vinylenedipyridine, 4,4'-stilbenedicarboxylic acid, β-pinene.

Preference is also given to reacting unsaturated compounds of the formula IIb

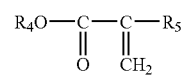

in which
$R_4$ is methyl or ethyl and $R_5$ is methyl, ethyl or the ethoxycarbonyl radical, to give the correspondingly preferred carbonyl compounds. Very particular preference is given to reacting compounds in which $R_4$ and $R_5$ is methyl.

Examples of starting compounds of the formula IIb are methyl methacrylate, ethyl alkylacrylate or diethyl methylenemalonate.

A further preferred group of starting materials for the preparation of the correspondingly preferred carbonyl compounds of the formula I are compounds of the formula IIc

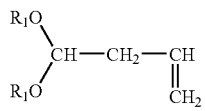

in which $R_1$ is as defined in formula I. Examples of compounds of the formula IIc are 4,4-dimethoxybutene or 4,4-di-n-butoxybutene.

In addition, in a preferred manner, compounds of the formula IId

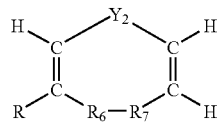

in which $Y_2$ is an o-phenylene radical or an alkylene radical having 2 to 4 carbon atoms and $R_6$ and $R_7$ are together a single bond between the adjacent carbon atoms or an alkylene radical having 2 to 4 carbon atoms, are reacted to give the correspondingly preferred dialdehydes of the formula I. Examples of compounds of the formula IId are naphthalene or cyclooctadiene (1,5).

Finally, a further group of unsaturated compounds of the formula IIe

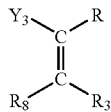

in which
if R and $R_3$ are each H, $Y_3$ and $R_8$ are together an alkylene radical having 2 to 6 carbon atoms or the radicals

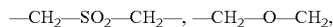

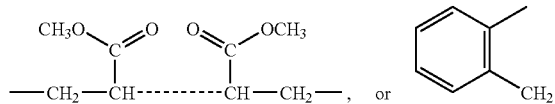

is reacted, in a preferred way, to give the correspondingly preferred dialdehydes of the formula I, or if R and $R_3$ are each $COOR_1$ and $Y_3$ and $R_8$ are H, to give the correspondingly preferred glyoxylic esters, their hemiacetals or monohydrates of the formula I.

Examples of compounds of the formula IIe are cyclohexene, cyclooctene, cyclododecene, sulfolene, indene, dimethyl tetrahydrophthalate or 2,5-dihydrofuran, and also dimethyl or diethyl maleate, monophenylmenthyl maleate, monomenthyl, fenchyl or boneyl maleate, and the analogous fumaric esters.

Thus, for the process according to the invention a very wide variety of compounds are suitable, including those which may also contain complex structures with a very wide variety of functionalities. Thus, in addition to the preferred starting compounds already mentioned, compounds with complex structures, such as, for example, cephalosporins etc. are also suitable as starting material. The only prerequisite or limitation for choosing the reactant is the presence of at least one double bond which can be cleaved by ozone.

The ozonization according to the invention is carried out at temperatures of –80° C. to just below the explosion limit of the solvent used, i.e. up to 100° C., depending on the solvent used. The temperature is, again depending on the solvent used, –30 to +80° C., the maintenance of a temperature of from –20 to +50° C. again being particularly preferred. The ozonolysis can be carried out at atmospheric pressure or under pressure.

The reaction of the unsaturated compounds with ozone in stage a) is carried out in an organic solvent in which the starting compounds are readily soluble or in an aqueous solution.

Suitable organic solvents are, accordingly, alcohols, carboxylic acids, hydrocarbons etc. Preferred solvents are lower aliphatic alcohols having 1 to 6 carbon atoms, such as methanol, ethanol, isopropanol, etc., the use of methanol and ethanol being particularly preferred, or mixtures with non-halogenated hydrocarbons.

In the preparation of, for example, glyoxylic ester hemiacetals of the formula I, the alcohol used as solvent is important insofar as this alcohol participates in the acetal formation.

The ozonization step can, however, also be carried out in aqueous solution, depending on the reactant used. If the starting compound is itself insoluble in water, the salts thereof are used. In this connection, suitable salts are all those which lead to water-soluble compounds. Examples thereof are alkali metal or alkaline earth metal salts, such as, for example, sodium, potassium, calcium or magnesium salts. It is, however, also possible to prepare the aqueous solution of the corresponding salt of the starting compound chosen by adding a suitable acid or base. Preferred acids are mineral acids, such as sulfuric acid, nitric acid or phosphoric acid.

The reaction with ozone takes place continuously according to the invention, where ozone is used, depending on the reactivity of the reactants and substrates, relative to the solvent used, in stoichiometric amounts up to a 40% excess. Preference is given to using stoichiometric amounts up to a 20% excess of ozone.

In a first variant, equipment is used which consists of two absorption apparatuses, devices for dissipating the heat of the reaction, such as, for example, external or internal heat exchangers, and devices for separating the gas phase from the liquid phase.

The reactant streams here are countercurrent. The starting material is fed into the first absorption apparatus, the starting concentration depending on the reactant used and the reaction conditions and preferably being between 1 and 3 mol/l, based on the double bonds, particularly preferably between 1.2 and 2 mol/l, based on the double bonds; the ozone-bearing $O_2$ stream is, by contrast, introduced into the second absorption apparatus. The amount of ozone is chosen here, depending on the reactivity of the reactant, such that, for reactive substances, it preferably corresponds to a virtually stoichiometric ozone consumption up to a about 107% of the stoichiometric amount and, for less reactive substances, an ozone consumption of about 107 to 140%, preferably up to 120%, of the stoichiometric amount based on the starting compound.

In the first absorption apparatus, the reactant used is brought into contact with the ozone stream which, after passing through the second absorption apparatus, is fed into the first absorption apparatus. In this apparatus, there is a deficit of ozone since there are large amounts of reactant present here, while the ozone content of the introduced stream is reduced by up to 95%, depending on the substrate and nature of the column, as a result of being used up by the reaction in the second absorption apparatus. Following the reaction of the ozone introduced into the first absorption apparatus with the correspondingly introduced reactant, the reaction mixture emerges from the first apparatus and is separated into a gas phase and a liquid phase. Virtually no ozone is present in the gas phase. The liquid phase, which now still comprises unreacted reactant, solvent and the corresponding ozonolysis product, is then fed into the second absorption apparatus into which, as has already been described above, the ozone-bearing $O_2$ stream with the given starting concentration of ozone is introduced. There is thus an excess of ozone in this apparatus, based on the reactant, since only a small percentage of the amount of reactant, based on the amount originally used, is present. The amount of reactant is accordingly nearly only 1 to 10%, preferably 1 to 5% and particularly preferably 1 to 3% of the starting concentration. In contrast, in the second absorption apparatus, large amounts of ozonolysis product, obtained by the reaction in the first absorption apparatus, are already present in the second absorption apparatus.

Surprisingly, the introduced ozone reacts, despite the low concentration of reactant and the high concentration of ozone product, more quickly with the residual amounts of reactant than with the ozonolysis product or the solvent, meaning that, even at these concentration ratios, the high yield losses expected by the person skilled in the art do not actually arise.

When the reaction is complete, the reaction mixture emerges from the second absorption apparatus and is again separated into a gas phase and a liquid phase. As described above, the gas phase contains only a small percentage of ozone, which is introduced into the first apparatus for further reaction of newly introduced reactant. The liquid phase, which now contains only the corresponding ozonolysis product in the solvent used is then passed to the work-up stage (hydrogenation, oxidation or heating).

This variant is preferably used for reactants which react rapidly relative to the solvent or to the ozonolysis product formed.

In a further variant, the reactant stream is again fed into the first absorption apparatus. In this procedure, the ozone-bearing $O_2$ stream is also introduced into the first apparatus, but some of the stream is also split off for the second apparatus and introduced into it (ozone split). The ozone-bearing $O_2$ stream is split here in a ratio of first apparatus to second apparatus of from 50:50 to 90:10, preferably from 70:30 to 85:15.

The $O_2$ stream introduced into apparatus 1 and 2 comprises about 4–10%, preferably 5–8%, of ozone. Accordingly, in the first absorption apparatus, there is again a deficit of ozone since large amounts of reactant are present in this apparatus. The reactant concentration, based on the double bonds, after passing through the first absorption apparatus, depends on the splitting ratio of the ozone stream and, for a 50:50 split, is preferably 0.9 to 2 mol/l and particularly preferably 1 to 1.5 mol/l and, for a 90:10 split, is preferably 0.1 mol/l to 0.5 mol/l, particularly preferably 0.1 to 0.3 mol/l.

When the reaction is complete, the reaction mixture emerges from the first absorption apparatus and is separated into a gas phase and a liquid phase, the gas phase comprising only a small percentage of ozone. The liquid phase, which comprises mainly the corresponding ozonolysis product in the solvent used and residual, unreacted reactant in a concentration of only 5 to 50%, preferably 10 to 50%, of the starting concentration, is then introduced into the second absorption apparatus, where it is brought into contact with the ozone stream split off as described above. In the second absorption apparatus, there is an excess of ozone since, as described, only small amounts of reactant pass into the second apparatus. Despite ozonolysis product and solvent, which actually have a high tendency to react with ozone, in essentially larger amounts compared with the reactant, the unreacted reactant nevertheless reacts with the introduced ozone.

When the reaction is complete, the reaction mixture emerges from the second absorption apparatus and is again separated into a gas phase and a liquid phase. No or negligibly small amounts of ozone are present in the gas phase. The liquid phase, which now comprises only the corresponding ozonolysis product in the solvent used, is then passed to the work-up phase (step b).

This variant is preferably used for substrates which react slowly.

In one modification of this variant, the offgas from the first absorption apparatus can be mixed with the split-off partial stream, as result of which it is diluted. In this case, an oxygen saving in the case of the ozone-bearing $O_2$ stream is achieved. Furthermore, the overall ozone consumption is somewhat reduced.

It is further possible to introduce only the offgas stream from the first absorption apparatus into the second apparatus and to dispense with the splitting of the original ozone-bearing $O_2$ stream, meaning that the entire ozone-bearing $O_2$ stream is fed into the first apparatus. This results both in a reduction in the ozone deficit in the first absorption apparatus, and also in the ozone excess in the second apparatus.

In the case of very reactive reactants, it is also possible to carry out the ozonization in only one step, i.e. in only one absorption apparatus.

For all ozonization variants, it is also possible to replenish reactant with uninterrupted ozonization, as soon as the content of reactant has dropped to a predetermined value, so that the content is kept constant at this value during the ozonization.

In the ozonization according to the invention, absorption apparatuses are understood as meaning customary apparatuses which effect a gas-liquid exchange, such as, for example, absorption columns, bubble columns, stirred reactors, stirred-tank reactors, mixers, loop reactors etc.

In a further preferred embodiment, the continuous ozonolysis is carried out in two bubble columns as absorption apparatuses. The ozone stream can here be again passed countercurrently, as in the variant for rapidly reacting substrates, although the ozone-split is preferably used.

The combination of bubble columns as absorption apparatuses and ozone-split is particularly suitable for slowly reacting the substrates and for reactions in the aqueous system, for example for the ozonolysis of quinoline in the aqueous system.

The continuous ozonolysis according to the invention is characterized by its simple process control. Particular advantages are that it does not result in ozone interruptions when changing batches, and the amount or concentration of ozone upon breakthrough, i.e. when the reaction is complete, can be readily controlled. As a result of this continuous procedure, moreover, the amounts of peroxide in the reaction solution are kept lower compared with the prior art. The reaction mixture leaving the circulation apparatus for the ozonolysis has a peroxide content of from 1 to 2 mol/l, preferably from 1 to 1.5 mol/l.

According to the invention, the continuous ozonolysis is followed by the work-up of the peroxide solution, which depends on the reaction conditions chosen during the ozonolysis. If the ozonolysis is carried out in aqueous or mineral-acidic, aqueous solution, then the peroxides obtained by the ozonolysis can be converted into the corresponding end products, for example, by simple heating. This is the case particularly if substituted quinolines are converted into the corresponding substituted pyridinecarboxylic acids, such as, for example, into 2-acetylnicotinic acid. Preference is given here to bubbling in oxygen, in the form of pure oxygen or in the form of air, at the same time, so that the formation of secondary products is prevented.

In other cases, an oxidation step is necessary after the ozonolysis in order to obtain the desired end-products. For this purpose, the peroxide solution is treated with a suitable oxidizing agent, for example with hydrogen peroxide, hypochloride, peracids, peroxodisulfate, etc.

If stilbene compounds are used as starting materials, then a mixture of corresponding aldehyde and hydroperoxide is present after the ozonolysis. The peroxide can be decomposed either under acidic conditions or under alkali conditions. If the aldehyde is the desired end-product, then this product is isolated from the mixture. If the corresponding acid is the desired product, another oxidation step is carried out.

If the ozonolysis is carried out not in aqueous solution, but in an organic solvent, then the ozonolysis is followed by continuous hydrogenation. In this connection, it is merely decisive that the peroxidic ozonolysis products are present in at least partially dissolved form in an organic diluent which is inert under the reaction conditions of the hydrogenation. In addition to the solvents used in the nonaqueous ozonolysis, organic diluents are also to be understood as meaning customary diluents used during the hydrogenation, such as, for example, aliphatic or aromatic, optionally chlorinated, hydrocarbons, such as pentane, hexane, cyclohexane, toluene, xylene, methylene chloride, dichloroethane, chlorobenzenes, carboxylic esters, such as methyl, ethyl or butyl acetates, ethers and ketones, provided they are not able to form peroxides which are unacceptable from a safety view point, and also alcohols, such as methanol, ethanol, isopropanol. When alcohols are used as diluents, the products which may form are not only the aldehydes or ketones corresponding to the olefins used, but also their hemiacetals, acetals or their ketals, the acetalization or ketalization essentially being dependent on the pH conditions.

In the process according to the invention, preference is given to using peroxidic ozonolysis solutions in a lower, aliphatic alcohol having 1 to 6 carbon atoms, particularly preferably in methanol or ethanol. However, surprisingly, the concentration of the peroxides in the solution is not of importance for the process according to the invention. In general, the solutions of the peroxidic ozonolysis products, which are obtained by the above-described, continuous ozonolysis, have a peroxidic concentration of less than 2, preferably of less than 1.5 mol/l. Since peroxides in relatively high concentrations have a tendency for explosion-like decomposition, it is therefore preferably to be observed that the solutions used have a peroxide concentration below 2 mol/l, particularly preferably below 1.5 mol/l.

The catalytic hydrogenation of the ozonolysis product which follows the ozonization is carried out in the process according to the invention in dilute solution, where, optionally with suitable measures and devices therefor, care is taken that during the overall hydrogenation a peroxide content in the hydrogenation solution of below 1.5 mol/l, preferably of below 1 mol/l, particularly preferably of below 0.1 mol/l, very particularly preferably of at most 0.05 mol/l and in particular of at most 0.02 mol/l is set and maintained.

To carry out the process in practice, a suspension of the catalyst in the alcohol used in stage a) for the ozonization, preferably a methanol or ethanol, very preferably methanol, is introduced into a hydrogenation reactor, and the solution obtained during the ozonization is continuously fed in by means of a controllable metering device. When adding the ozonolysis solution at the start and during the course of the hydrogenation, it is of course necessary to ensure that the peroxide content in the hydrogenation solution given above is not exceeded as a result of the added amount of the peroxide-containing ozonization products.

As a result of the low concentration of peroxide-containing ozonization products during the actual hydrogenation operation, the quantitative ratio of catalyst to the substrate to be reduced is uniformly favorable through the entire duration of the hydrogenation, meaning that even when the catalyst is used sparingly, a rapid reduction is ensured. In this way, the poisoning which is otherwise observed at high peroxide concentrations, and the loss in activity of the catalyst associated therewith is also prevented.

Viewed overall, however, as a result of the continuous feed, a large amount of ozonization products can be reductively cleaved in a relatively small volume, as a result of which, in the end stage of the process, concentrated solutions form and, as well as solvent itself, time and costs for the distillative removal of the solvent during work-up can be saved. Suitable catalysts are the noble metal catalysts customarily used for hydrogenations, which can be used in the form of powder catalysts with support material or without support material. Preference is given to using palladium or platinum catalysts, in particular platinum catalysts without support material. In the case of powder catalysts, suitable support materials are, for example, carbon, aluminum, silica gel or kieselguhr. It is also possible to use monolith catalysts. A monolith catalyst is to be understood as meaning a catalyst which consists of a support coated with a catalyst base material. The support preferably has as large a surface area as possible, which can be achieved, for example, by honeycomb or lamellar structuring. The support is in the form of one piece and can consist of materials suitable for this purpose, for example of metal, glass, ceramic, plastic. Preference is given to a metal support, for example made of steel, aluminum, since it has been found that this uniformly absorb the heat of the reaction and dissipate it again into the surrounding reaction medium. This is because it has been found that the use of nonconductive materials as support may lead to local overheating in the reaction medium, meaning that yields and purity of the reaction products can be impaired. Catalyst base substance is to be understood as meaning catalyst base substances which are customary for the reduction of organic peroxide solutions. Examples of customary catalysts base substances are noble metals, such as platinum, palladium, transition metals, such as nickel, cobalt, rhodium, the oxides thereof, or mixtures of such metals or metal oxides. In this connection, these metals can be partially poisoned by heavy metals such as lead, bismuth. In the process according to the invention, preference is given to using noble metals or mixtures of noble metals with transition metals as catalyst base substance. In the process according to the invention, the yields are per se independent of the amount of catalyst used, although it is recommended, to achieve a sufficient hydrogenation rate, to initially introduce said catalysts in noble metal amounts of from 0.1 to 5% by weight, preferably from 0.5 to 2% by weight, based on the total amount of ozonization products introduced in each case per hour.

In the process according to the invention, equivalent amounts of hydrogen are consumed for the reduction of the ozonization products. The amount of hydrogen which can be used during the hydrogenation ranges from one mole equivalent to a manifold molar excess. The use of excess hydrogen does not afford any advantages and is only expedient in order to ensure an adequate supply of hydrogen to the hydrogenation mixture.

In the process according to the invention, the hydrogenation can be carried out under virtually pressureless conditions. Virtually pressureless conditions are to be understood here as meaning pressures of from 1 to about 3 bar, as is customary in the art, in order to prevent the penetration of air into the hydrogenation reactor. In this way, the reduction of the ozonization products can be carried out very simply in technical and apparatus terms. It is, however, also possible to carry out the hydrogenation at a pressure up to 20 bar, thereby increasing the rate of hydrogenation.

The reductive cleavage generally proceeds exothermically and is carried out at temperatures of from $-10$ to $+150°$ C., depending on the product, and according to a preferred embodiment of the present invention at $+15$ to $+70°$ C. and particularly preferably at temperatures in the range from $+20$ to $+50°$ C.

Preference is given to maintaining a pH of from 2 to 5 during the hydrogenation. Since acidic secondary products can form in small amounts during the course of the hydrogenation, a base, preferably dilute sodium hydroxide solution, may optionally be added in a metered way to maintain the desired pH.

When the hydrogenation is complete, under the conditions of the process according to the invention, a preferably alcoholic solution of the process products is obtained, which is virtually peroxide-free and can be worked-up in a risk-free manner.

For the continuous hydrogenation according to the invention, all hydrogenation reactors which ensure adequate mass transfer of hydrogen into the liquid phase are suitable.

These may, for example, have tubular reactors of very diverse construction, such as, for example, stirred-tank reactors, loop reactors, etc. Suitable stirrers, such as, for example, 3-paddle stirrers, injectors etc. It is, however, also possible to use stirred or unstirred bubble columns, fixed-bed reactors etc.

In the process according to the invention, in one variant the peroxide-containing ozonolysis product solution obtained from the ozonolysis stage, and the stream of hydrogen is passed into the hydrogenation apparatus. The hydrogenation apparatus consists here, for example, of a stirred reactor, fitted with a 3-paddle stirrer, hydrogen inlet, hydrogen measurement, pH measurement, temperature measurement, cooling, filtration device and metering pumps. The desired solvent and the catalyst used, preferably no monolith catalyst, are initially introduced. The peroxide solution is then fed in with stirring, preferably with vigorous stirring with the continuous introduction of hydrogen gas. The desired peroxide content can be regulated via the dosing rate. Where appropriate, the addition of a base for regulating the pH can be carried out simultaneously. The volume of the reaction solution is kept constant by level-adjusted discharge via the filtration unit, where the peroxide content of the discharged solution is continually monitored. The peroxide content of the separated-off solution is here below 0.01 mo/l. In contrast to the prior art, it is not necessary here to separate off the catalyst since the catalyst, if a suitable filtration unit is chosen, is not discharged with the product solution, but is again returned to the reaction vessel. Particularly suitable filtration units are, accordingly, cross-flow filtration apparatuses which are equipped, for example, with metal frits in the form of sintering tubes, or immersed metal frits.

As a result of the process control according to the invention, it is thus possible to use the catalyst for years since chemical poisoning does not occur. Only mechanical wear becomes noticeable upon use for years. In addition, the peroxides are reacted rapidly and reliably.

Step b) can be carried out continuously or else discontinuously.

EXAMPLE 1

COMPARATIVE EXAMPLE A: BATCH a) Ozonization:

A continuous circulation apparatus consisting of an absorption column, separation vessel, recirculation pump and external heat exchanger was charged with 4 liters of a methanolic solution of 900 g of DMM (content of 225 g/l, corresponding to 1.56 mol/l). The temperature was cooled to $-20°$ C. by cooling via the external heat exchanger. The recycle amount was about 220 l/h.

The solution was brought into contact with 2500 l/h (STP) of ozone/oxygen stream with an ozone content of 55 g/Nm$^3$ in the absorption column and reacted with the ozone present. The exothermic reaction took place virtually immediately, and all of the ozone was taken up. In the separation vessel at the foot of the absorption column, the mixture separated into a liquid phase and a gas phase.

When the ozonolysis was complete, the DMM content was about 2 g/l, corresponding to 1% of the starting amount.

The amount of ozone taken up was determined and was overall about 305 g, corresponding to 102% of theory.

b) Hydrogenation:

The solution obtained in the ozonolysis was divided into portions and was fed, via a dosing vessel, into a hydrogenation reactor into which a suspension of 1.5 g of Pt Adams catalyst, prepared by hydrogenation of PtO$_2$, in 0.5 liter of methanol had been introduced and which had been filled with hydrogen, in doses such that the peroxide content in the hydrogenation reactor at the start and over the course of the entire hydrogenation was at most 0.1 mol/l. Hydrogenation was continued with vigorous stirring and the addition of hydrogen until the peroxide sample was negative, a temperature of 30° C.–33° C. and, by adding methanolic NaOH, a pH of from 2 to 4 being maintained over the entire hydrogenation period.

The contents of the hydrogenation reactor were then drawn off with suction via a frit until the residue was 0.5 liters, solution ozonized afresh was fed into the reactor via the metering vessel, and the hydrogenation operation was repeated under the reaction conditions given above.

When the hydrogenation was complete, a polarographically determined methyl glyoxylate-methanol hemiacetal content of 12.125 mol (97% of theory) was established. For work-up, NaOH present in bonded form in the hydrogenation mixture was carefully precipitated out by cooling with 98% strength $H_2SO_4$ as $Na_2SO_4$ and separated off by filtration. The methanol was then removed on a rotary evaporator and the residue was distilled at about 55° C. and 25 Torr. The yield of pure methyl glyoxylate-methanol hemiacetal was 1425 g (11.87 mol), corresponding to 95% of theory.

EXAMPLE 2 a) Ozonization 4 liters of methanolic DMM solution were ozonized as described in Example 1 in the recirculation apparatus from Example 1. As soon as the DMM content had dropped to 2 g/liter, further DMM solution was fed in, with uninterrupted $O_3$ introduction, at the same concentration as in Example 1 such that the DMM content was kept constant between 2 and 3 g/liter. In this way, a total of 16 liters of methanolic peroxide solution were obtained, 3600 g of DMM were ozonized.

The total amount of ozone taken up was 1450 g, corresponding to 30.25 mol=121% of theory. The ozone consumption is significantly greater compared with Example 1, ozone was consumed in the secondary reactions.

b) Hydrogenation:

The solution obtained in the ozonolysis was fed, via a metering vessel, into a hydrogenation reaction into which a suspension of 1.5 g of Pt in 0.5 liter of methanol had been introduced and which had been filled with hydrogen, at a metering rate such that the peroxide content in the hydrogenation reactor at the start and over the course of the entire hydrogenation was at most 0.01 mol/l. The consumed hydrogen was continually topped up by means of pressure regulation. Here, over the entire hydrogenation period, a temperature of 30° C.–33° C. was maintained by cooling, and a pH of from 2 to 3 was maintained by adding methanolic NaOH. As soon as the hydrogenation reactor was full, hydrogenated solution was continuously taken off via an immersed frit in order to keep the level virtually constant. During this, the metered addition of the peroxide solution was not interrupted. The peroxide content was controlled continually by iodometric titration. When the hydrogenation was complete, the hydrogenation reactor was emptied via the frit and a polarographically determined methyl glyoxylate-methanol hemiacetal content of 5100 g=42.5 mol (85% of theory) was established.

EXAMPLE 3 a) Ozonization:

In a recirculation apparatus as described in Example 1, 16 liters of a solution of 3600 g of DMM in methanol were ozonized in 4 parts each of 4 liters until the DMM content had dropped to about 40 g/l. The peroxide solution obtained in this way was stored in a deep-freeze at about −30° C. During storage, neither an exothermic reaction nor a decrease in the peroxide content was established.

In the second stage of the ozonization, the stored peroxide solution was ozonized analogously to Example 2 to a DMM content of 2–3 g/l. In this way, a total of 16 liters of methanolic peroxide solution were obtained, and 3600 g of DMM were ozonized. The total amount of ozone taken up was 1252 g, corresponding to 26.1 mol=104% of theory.

b) Hydrogenation:

The solution obtained in the ozonolysis was fed, via a metering vessel, into a hydrogenation reactor into which a suspension of 1.5 g of Pt in 0.5 liter of methanol had been introduced and which had been filled with hydrogen, at a metering rate such that the peroxide content in the hydrogenation reactor at the start and over the course of the entire hydrogenation was at most 0.01 mol/l. The consumed hydrogen was continually topped up by means of pressure regulation. Here, over the entire hydrogenation period, a temperature of 30° C.–33° C. was maintained by cooling, and a pH of from 2 to 3 was maintained by adding methanolic NaOH. As soon as the hydrogenation reactor had been filled, hydrogenated solution was drawn off continuously via an immersed frit in order to keep the level virtually constant. During this, the metered addition of the peroxide solution was not interrupted. The peroxide content was continually controlled by iodometric titration.

When the hydrogenation was complete, the hydrogenation reactor was emptied via the frit, and a polarographically determined methyl glyoxylate-methanol hemiacetal content of 48 mol (96% of theory) was established.

EXAMPLE 4 a) Ozonization:

In a recirculation apparatus as described in Example 3, 16 liters of a solution of 3600 g of DMM in methanol were ozonized, although this time until the DMM (dimethylmaleate) content had dropped to about 120 g/l. The peroxide solution obtained in this way was stored in a deep-freeze at about −30° C. During storage, neither an exothermic reaction nor a decrease in the peroxide content was established.

In the second stage of the ozonization, the stored peroxide solution was ozonized analogously to Example 2 to a DMM content of 2–3 g/l. In this way, a total of 16 liters of methanolic peroxide solution were obtained, and 3600 g of DMM were ozonized. The total amount of ozone taken up was 1288 g, corresponding to 26.8 mol=107% of theory.

b) Hydrogenation:

The solution obtained in the ozonolysis was fed, via a metering vessel, into a hydrogenation reactor into which a suspension of 1.5 g of Pt in 0.5 liter of methanol had been introduced and which had been filled with hydrogen, at a metering rate such that the peroxide content in the hydrogenation reactor at the start and over the course of the entire hydrogenation was at most 0.01 mol/l. The consumed hydrogen was continually topped up by means of pressure regulation. Here, over the entire hydrogenation period, a temperature of 30° C.–33° C. was maintained by cooling, and a pH of from 2 to 3 was maintained by adding methanolic NaOH. As soon as the hydrogenation reactor had been filled, hydrogenated solution was drawn off continuously via an immersed frit in order to keep the level virtually constant. During this, the metered addition of the peroxide solution was not interrupted. The peroxide content was continually controlled by iodometric titration.

When the hydrogenation was complete, the hydrogenation reactor was emptied via the frit, and a polarographically determined methyl glyoxylate-methanol hemiacetal content of 2748 g=47.9 mol (95.8% theory) was established.

EXAMPLE 5 a) Ozonization:

In a recirculation apparatus as described in Example 3, 4 liters of a solution of 900 g of DMM in methanol were ozonized, until the DMM content had dropped to about 40 g/l. Then, with uniform feed of ozone, a further 20 l of a solution with a cencentration of 225 g/l were metered in such a way that a DMM content of 40 g±2 g/l was retained in the ozonolysis solution. The level in the apparatus was kept constant by withdrawing the excess peroxide solution produced. The peroxide solution obtained in this way was stored in a deep freeze at about −30° C. During storage, neither an exothermic reaction nor a decrease in the peroxide content was established.

In the second stage of the ozonization, the stored peroxide solution was ozonized analogously to Example 2 to a DMM content of 2–3 g/l. In this way, a total of 24 liters of methanolic peroxide solution were obtained, and 5400 g of DMM were ozonized. The total amount of ozone taken up was 1900 g, corresponding to 39.6 mol=106% of theory.

b) The hydrogenation was carried out as in Example 4.

When the hydrogenation was complete, the hydrogenation reactor was emptied by the frit and a polarographically determined methyl glyoxylate-methanol hemiacetal content of 8640 g (yield 96.0% of theory) was established.

EXAMPLE 6

COMPARATIVE EXAMPLE B: OZONOLYSIS BATCH HYDROGENATION CONT.

a) Ozonization:

A peroxide solution was prepared by ozonolysis of naphthalene in methanol analogously to Example 1. For this, 256 g of naphthalene were ozonized in 4 liters of methanolic solution. The initially undissolved naphthalene dissolved over the course of the ozonization.

b) Hydrogenation:

The solution obtained in the ozonolysis was fed, via a metering vessel, into a hydrogenation reactor into which a suspension of 1.5 g of Pt in 0.5 liter of methanol had been introduced and which had been filled with hydrogen, at a metering rate such that the peroxide content in the hydrogenation reactor at the start and over the course of the entire hydrogenation was at most 0.01 mol/l. The hydrogen consumed was continually topped up by means of pressure regulation. During this, over the entire hydrogenation period, a temperature of 30° C.±2° C. was maintained by cooling, and a pH of from 2 to 4 was maintained by adding methanolic NaOH. As soon as the hydrogenation reactor was full, solution hydrogenated continuously was taken off via an immersed frit in order to keep the level virtually constant. During this, the metered addition of the peroxide solution was not interrupted.

When the hydrogenation was complete, a content of ortho-phthalaldehyde of 220.5 g (82.3% of theory) was established. The solution was set at pH 1 for work-up with $H_2SO_4$. After 4 hours, the acetalization was complete. The methanolic acetal solution was added dropwise to an excess hydroxide solution, and the methanol was distilled off simultaneously. The acetal was extracted twice from the reaction mixture using MTBE, and the solvent was removed on a rotary evaporator. This left a residue of phthalaldehyde-dimethylacetal. The weight was 293.3 g, corresponding to 81.5% of theory.

EXAMPLE 7 a) Ozonization:

In the recirculation apparatus from Example 1, 4 liters of 0.5 molar methanolic naphthalene solution were ozonized as described in Example 2. As soon as the naphthalene content had dropped to 2 g/l, a further 0.5 mol of naphthalene solution was fed in, with uninterrupted $O_3$ introduction, so that the naphthalene content was kept constant between 2 and 3 g/liter. In this way, a total of 8 liters of methanolic peroxide solution were obtained, and 512 g of naphthalene were ozonized.

The total amount of ozone taken up was 495 g, corresponding to 10.31 mol=129% of theory.

b) Hydrogenation:

The hydrogenation was carried out continuously as in Example 6.

When the hydrogenation was complete, a content of ortho-phthalaldehyde of 160.7 g (60% of theory) was established by GC.

EXAMPLE 8 a) Ozonization:

In a recirculation apparatus as described in Example 3, 8 liters of a solution of 512 g of naphthalene in methanol were ozonized until the naphthalene content had dropped to about 20 g/l. The peroxide solution obtained in this way was stored in a deep-freeze at about −30° C. During storage, neither an exothermic reaction nor a decrease in the peroxide content was established.

In the second stage of the ozonization, the stored peroxide solution was ozonized analogously to Example 2 to a naphthalene content of 2–3 g/l. In this way, a total of 8 liters of methanolic peroxide solution were obtained.

The total amount of ozone taken up was 458 g, corresponding to 9.54 mol=119% of theory.

b) Hydrogenation:

The hydrogenation was carried out continuously as in Example 6.

When the hydrogenation was complete, a content of ortho-phthalaldehyde of 417.9 g (78% of theory) was established.

EXAMPLE 9

COMPARATIVE EXAMPLE C 4 liters of a solution of 600 g of methyl methacrylate in methanol with an addition of 0.1 g of hydroquinone to prevent polymerization, were ozonized as in Example 2 to an MMA content of 1 g/l and then hydrogenated with a Lindlar catalyst 5% Pd/Pb on $CaCO_3$ at pH 5. Some of the methyl methacrylate used was discharged during the ozonolysis by the $O_2$ off gas. The ozone consumption was, at 266 g, only 92% of theory. Following the hydrogenation, the methyl pyruvate present in the solution was determined as 528 g, corresponding to 86.3% of theory, based on methyl methacrylate used.

EXAMPLE 10

In a recirculation apparatus, a minimal volume of 1.5 l of methanol with a concentration of 2 g/l of methyl methacrylate was initially introduced, and the ozonization and the metered addition of 4 liters of an MMA solution of concentration 150 g/l were started simultaneously, such that the methyl methacrylate (MMA) content remained constant roughly in the range 1 g/l±1 g/l.

A total of 603 g of methyl methacrylate were ozonized, and the ozone consumption was 283 (98% of theory).

The hydrogenation was carried out analogously to Example 9. In the hydrogenation solution, 567.8 g of methyl pyruvate were found. (92.8% of theory)

EXAMPLE 11

In a recirculation apparatus, a minimal volume of 1.5 l of methanol with a concentration of 20 g/l of methyl methacrylate was initially introduced, and the ozonization and the metered addition of 8 liters of an MMA solution of concentration 150 g/l were started simultaneously, so that the MMA content remained constant roughly in the range 20 g/l±1 g/l. The peroxide solution resulting from the ozonolysis was stored at −30° C. for the second stage of the ozonolysis. In the second stage of the ozonolysis, 1.5 l of peroxide solution from Stage 1 were initially introduced and ozonized to a concentration of about 1 g/l of methyl methacrylate. Then, with continuing ozonolysis, the peroxide solution from Stage 1 was metered in so that the concentration of methyl methacrylate was kept constant at 1 g/l±1 g. The peroxide solution was withdrawn continuously from the apparatus so that the level of solution in the apparatus remained approximately constant.

A total of 1230 g of methyl methacrylate was ozonized, and the ozone consumption was 562 (95% of theory)

The hydrogenation was carried out analogously to Example 9. In the hydrogenation solution, 1148 g of methyl pyruvate were found. (91.5% of theory, based on methyl methacrylate used).

EXAMPLE 12

COMPARATIVE EXAMPLE D

Methyl methacrylate was ozonized as in Example 9 and continuously hydrogenated, although the catalyst used was platinum sponge, obtained by hydrogenation of 3 g of $PtO_2$. The hydrogenation was carried out as in Example 9 at pH 5. Inclusive of the rinse solutions, 4.6 liters of a methanolic solution were obtained, which comprised 549 g of methyl lactate. (88.1% of theory based on methyl methacrylate and 95.7% based on ozone used).

EXAMPLE 13

4 liters of a solution of 600 g of methyl methacrylate were ozonized analogously to Example 10 and hydrogenated as in Example 12. In the hydrogenation solution, 580 g of methyl lactate (93% of theory based on methyl methacrylate used) were found.

EXAMPLE 14

COMPARATIVE EXAMPLE E 4 liters of a solution of 440 g of cyclooctene in methanol were ozonized as in Example 1. Immediately at the start of the ozonolysis there was considerable mist formation in the offgas. The mist formation was largely independent of the zone concentration, but did not arise when pure oxygen without ozone was used. The ozonolysis was interrupted for reasons of safety and the apparatus was emptied and cleaned.

EXAMPLE 15

4 liters of a solution of 440 g of cyclooctene (4 mol) in methanol were prepared. As described in Example 10, 1.5 liters of methanol were initially introduced, and 30 ml of cyclooctene solution were metered in, giving about 2 g/l of cyclooctene. The metered addition was stopped and then the ozonization was started with the simultaneous metered addition of cyclooctene solution. Sufficient cyclooctene was metered in for a cyclooctene concentration of 2 g/l±1 g/l to be maintained in the ozonolysis solution. Mist formation in the offgas was not observed at this concentration. The ozone consumption was 92 g (96 of theory).

The peroxide solution was continuously hydrogenated as in Example 2. 5.2 liters of a methanolic solution containing 522 g of octanedial (92% of theory, based on cyclooctene used) were obtained. The solution was adjusted to pH 1 with sulfuric acid, left to stand overnight at room temperature and adjusted to pH 10 with NaOH. 1 liter of water was then added, and the methanol was removed at a water-bath temperature of 100° C. using a rotary evaporator. The organic phase was separated off from the two-phase residue, the aqueous phase was extracted with 1×100 ml of MTBE, the organic phase was combined, dried with $Na_2SO_4$ and fractionated under reduced pressure. 855 g of 1,1,8,8-tetramethoxyoctane of $Kp_{30}$=147–149° C. were obtained (91% of theory).

EXAMPLE 16

4 liters of a solution of 417 g (4 mol) of vinylpyridine in methanol were ozonized analogously to Example 15, a concentration of about 2 g of vinylpyridine per liter being maintained by continuously metering in vinylpyridine solution in the ozonolysis. At this concentration, the uptake of ozone is still quantitative. The uptake of ozone is 196 g (102% of theory). The hydrogenation was carried out batchwise without pH regulation at 20° C. over 4 g of 10% Pd catalyst on activated carbon as described in Example 1. The product solution was analyzed by gas chromatography and the yield of pyridine aldehyde was determined as 347 g (81% of theory).

EXAMPLE 17

8 liters of a solution of 834 g of vinylpyridine in methanol were ozonized in a first stage as in Example 11 continuously at a vinylpyridine concentration of 20 g/l, and in a second stage at a vinylpyridine concentration of 2 g/l. The uptake of ozone is 380 g (98.9% of theory). The peroxide solution obtained was hydrogenated continuously without pH check at a maximum of 20° C. over 4 g of 10% pH catalyst on activated carbon. The product solution was analyzed by gas chromatography and the yield of pyridine aldehyde was determined as 720 g (84% of theory).

EXAMPLE 18

4 liters of a solution of 417 g (4 mol) of vinylpyridine in methanol were ozonized analogously to Example 16 and hydrogenated with 4 g of 10% Pd catalyst on activated carbon at at least 40±2° C. batchwise without the addition of hydroxide solution. The consumption of ozone was 196 g (102% of theory). The ozonized solution was fed into the hydrogen apparatus so that a peroxide content of 10 mmol was not exceeded. The pyridinealdehyde concentration formed in the process was less than 1%. The hydrogenated product solution was slowly introduced into excess aqueous sodium hydroxide solution, and the methanol was distilled off at the same time. In this step, pyridinealdehyde obtained in the hydrogenation was disproportionated to give hydroxymethylpyridine (HMP), and the simultaneously formed formaldehyde was disproportionated to give formate and methanol. The HMP was extracted from the resulting alkaline reaction mixture with 10×MTBE, the MTBE was distilled off from the organic phases, and the residue was fractionated at 80 mbar and 143° C. 332.1 g (76% of theory) of pure HMP were obtained as a colorless liquid.

EXAMPLE 19

12 liters of a solution of 1250 [lacuna] of vinylpyridine (12 mol) in methanol were prepared, and a 1 molar solution of vinylpyridine in methanol was ozonized analogously to Example 3, a concentration of 20 g of vinylpyridine per liter being maintained in the ozonolysis by metered addition. A total of 12 l of solution and thus 12 mol of vinylpyridine were fed in. All of the ozone introduced was taken up. The resulting peroxide solution was stored in a deep-freeze at −30° C. and used for a further continuous ozonolysis at a vinylpyridine content of about 2 g/l. The total ozone consumption was, at 570 g or 98.9% of theory, somewhat lower than in Example 18. The resulting peroxide solution was hydrogenated analogously to Example 17. After work-up analogously to Example 18, 1024 [lacuna] (78.1% of theory) of hydroxymethylpyridine were obtained.

EXAMPLE 20

COMPARATIVE EXPERIMENT F 4 liters of a solution of 220 g of cyclooctene in methanol were ozonized as in Example 1. Immediately at the start of the ozonolysis there was considerable mist formation in the offgas. The mist formation was largely independent of the ozone concentration, but did not arise when pure oxygen without ozone was used. The ozonolysis was interrupted as in Example 14 for reasons of safety and the apparatus was emptied and cleaned.

EXAMPLE 21

4 liters of a solution of 220 g of cyclooctene (4.07 mol) in methanol were prepared. The ozonization was carried out as described in Example 15, a maximum concentration of 2 g of cyclooctadiene being maintained in the ozonolysis solution. Mist formation in the offgas was not observed at this concentration. The ozone consumption was 190 g (97.3 of theory).

The peroxide solution was hydrogenated continuously as in Example 15. 5.2 liters of a methanolic solution were obtained. The overall yield was determined by oxime titration and revealed 330 g of succindialdehyde (94.3% of theory).

Characterization: the solution was treated with the molar amount of trimethylorthoformate, adjusted to pH 1 with sulfuric acid, left to stand overnight at room temperature and adjusted to pH 10 with NaOH. 1 liter of water was then added, and the methanol was removed at a water-bath temperature of 100° C. using a rotary evaporator. The organic phase was separated off from the two-phase residue, the aqueous phase was extracted with 3×100 ml of MTBE, the organic phase was combined, dried with $Na_2SO_4$ and fractionated under reduced pressure at 15 mbar.

486.5 g of 1,1,4,4-tetramethoxybutane of $Kp_{15}$=86–88° C. were obtained (90.5% of theory).

EXAMPLE 22

COMPARISON G

In a small-scale experiment, 1 molar solution of pinene in methanol was prepared and ozonized. Immediately at the start of the ozonolysis, mist formation arose in the offgas and the experiment was interrupted. The ozonization solution was diluted until mist formation was no longer observed. The adjusted concentration of pinene was about 28 g/l (=0.21 mol/l).

EXAMPLE 23

4 liters of a solution of 400 g of pinene in methanol were ozonized as in Example 15 with 130 g of ozone (92.3% of theory) and continuously hydrogenated at 30° C. and pH 4.5. The nopinone content in the hydrogenation solution was determined by gas chromatography as 363 g (89.6% of theory, based on pinene used). The hydrogen solution was treated with 1 l of water, adjusted to pH 5 with $H_2SO_4$, and the methanol was distilled off over a column. The resulting two-phase mixture comprised small fractions of a solid having an exothermic potential of about 1200 J/g. The mixture was therefore distilled with steam until the distillate was single-phase and the nopinone content in the distillate had dropped to below 2 g/l. The distillate was extracted with 2×MTBE, and the combined organic phases were fractionated. 356 g (87.6% of theory, based on pinene used) of pure nopinone were obtained.

EXAMPLE 24

4 liters of a solution of 900 g of butenediol (1,4) dibutyrate (3.94 mol) in methanol were ozonized as in Example 15 with 191 g of ozone (101% of theory) and continuously hydrogenated at 30° C. and pH 3.5. In the hydrogenation solution, the content of butyroxyacetaldehyde was determined as 933.8 g (91.0% of theory).

EXAMPLE 25

COMPARATIVE EXAMPLE H 4 liters of a methanolic solution of 470 g of sulfolene were ozonized as in Example 1 to a sulfolene content of <2 g/l and then hydrogenated as in Example 2 with 2 g of Adams catalyst at pH 3.5. The ozone consumption was, at 189 g, 99% of theory.

After the catalyst had been separated off, the oxime titration revealed a content of 568 g of 3-thiaglutaraldehyde 3,3-dioxide (95.1% of theory).

EXAMPLE 26

8 liters of a methanolic solution of 940 g of sulfolene were ozonized as in Example 15 to a sulfolene content of <2 g/l and then hydrogenated continuously as in the same example with 2 g of Adams catalyst at pH 3.5. The ozone consumption was with 388 g (101.6% of theory) and is thus somewhat higher than in Example 25.

After the catalyst has been separated off, the oxime titration reveals a content of 1140 g of 3-thiaglutaraldehyde 3,3-dioxide (94.8% of theory).

EXAMPLE 27

COMPARATIVE EXAMPLE I 4 liters of a solution of 300 g of 2,5-dihydrofuran (4.28 mol) in methanol were ozonized as in Example 1 with 163 g of ozone (79% of theory) and hydrogenated continuously at 30° C. and pH 3.5. Some of the dihydrofuran was discharged during the ozonolysis with the offgas stream.

In the hydrogenation solution, the content of 3-oxaglutaraldehyde was determined by oxime titration as 321 g (73.5% of theory).

EXAMPLE 28

8 liters of a solution of 600 g of 2,5-dihydrofuran (4.28 mol) in methanol were ozonized as in Example 2 with 398 g of ozone (96.9% of theory) and hydrogenated continuously at 30° C. and pH 3.5. The content of dihydrofuran in the offgas was below 2% of the feed amount.

In the hydrogenation solution, the content of 3-oxaglutaraldehyde was determined by oxime titration as 833 g (95.3% of theory).

EXAMPLE 29

Comparative Experiment PDC Batch in Recirculation Apparatus

Ozonization:

4 g of an aqueous solution of 240 g of quinoline (6% by weight, corresponding to 0.464 mol/kg) and 330 g of conc. sulfuric acid are introduced into a continuous recirculation apparatus, consisting of an absorption column, separation vessel, recirculation pump and external heat exchanger. The temperature is cooled to 0 to +3° C. by cooling via the external heat exchanger. The amount recirculated is about 220 l/h.

The solution is brought into contact with 2500 l/h (STP) of an ozone/oxygen stream with an ozone content of 96 g/$Nm^3$ in the absorption column and reacted with the ozone present. All of the ozone is not taken up. The concentration of unreacted ozone in the offgas was 26 g/$Nm^3$ at the start of the batch (corresponding to 27% of unreacted ozone) and 61 g/$Nm^3$ at the end of the batch (corresponding to 63.5% of unreacted ozone). In the separation vessel at the foot of the absorption column, the mixture separates into a liquid phase and a gas phase.

When the ozonolysis is complete, the quinoline content is about 0.7 g/l, corresponding to 1.1% of the starting amount.

The amount of ozone taken up was determined and was about 194 g overall, corresponding to 111% of theory.

Oxidation:

The solution obtained in the ozonolysis is treated, at 2 to 5° C., with 210 g of 30% $H_2O_2$ cooled to +5° C. As a result of the heat of the reaction, the temperature increases slowly and is maintained below 20° C. by cooling. PDC begins to crystallize even during the reaction. After 8 hours the reaction is complete.

The pH is adjusted to 1.5 and the reaction mixture is cooled to 0° C.

The precipitated PDC is filtered over a suction filter, washed with methanol and dried under reduced pressure at 40° C. to a constant weight. The yield of crystallized PDC is 217 g, corresponding to 71% of theory, and a further 30 g are present in the mother liquor.

The mother liquor is evaporated to one third of its volume under reduced pressure. After cooling to 0° C., filtration and drying, a further 24 g of PDC (8% of theory) are obtained. The yield of isolated PDC is thus 241 g (79% of theory), calculated based on quinoline. Total yield 247 g (81%).

EXAMPLE 30

PDC Continuously in Two Bubble Columns with Ozone Split

Ozonization was carried out in 2 bubble columns (2000 mm in length and 100 mm in diameter (total volume 15.7 liters)). The apparatus was equipped with a dosing pump to meter quinoline solution into the first bubble column and a further dosing pump to meter already ozonized solution from the first bubble column into the second bubble column. Each bubble column was provided with a device for metering fresh ozone.

Preparation: both bubbles were filled with 12 g of an aqueous sulfuric acid solution of quinoline (concentration as in Example 29). Ozone was then fed into the first bubble column to a quinoline content of 15 g/l, and into the second bubble column to a quinoline content of 1 g/l. The amount of gas was 10 $Nm^3$/h in each case, the pressure was 5.3 bar abs and the ozone content was 110 g/$Nm^3$.

Continuous operation: 3.5 $Nm^3$/h of ozone gas were fed into the second bubble column (with the low quinoline concentration), and 10 $Nm^3$/h of ozone gas were fed into the first bubble column. The quinoline concentration was kept between 0.8 and 1 g/l by metering reaction solution from the first bubble column into the second bubble column, the reaction solution withdrawn from the first column was replaced by the same volume of fresh quinoline solution, and by withdrawing a corresponding amount of already ozonized solution from the second bubble column, the volume of liquid therein was likewise kept constant. After a few hours, a uniform concentration of 12 g of quinoline/l was established in the first bubble column. In the first bubble column, 97% of the ozone used reacted, and in the second bubble column 95% of the ozone used reacted. No precipitation of PDC was observed. The ratios of the quinoline concentrations in the bubble columns corresponded reasonably accurately to the ratios of the amounts of ozone reacted.

The ozone consumption was measured and was about 107% of theory, calculated on the basis of quinoline. The ozone consumption was thus only slightly higher than the consumption in the case of the batch procedure under pressure.

1 kg of sample was taken in each case from the continuous operation at the start and at the end, this sample was oxidized and worked up as in Example 3 with $H_2O_2$.

The isolated PDC yield at the start of the continuous experiment was 58.8 g/kg of sample (77%) and 6.1 g/kg of sample (8%), corresponding to an isolated overall yield of 85%, and at the end was 58.4 g/kg of sample (76.5%) and 6 g/kg of sample (7.8%), corresponding to an isolated overall yield of 84.3%.

EXAMPLE 31

Comparative Experiment: PDC Continuously in the Recirculation Apparatus

A recirculation apparatus as in Example 29 was operated continuously:

4 kg of an aquoeus sulfuric acid solution of quinoline (composition: 6% by weight of quinoline, 9.1% by weight of sulfuric acid, remainder water as in Example 29) are ozonized with 2500 l (STP) of $O_2/O_3$ with 100 g of $O_3/Nm^3$ in a batchwise manner until the quinoline content had dropped to 0.9 g/l. Ozonization is then continued with the same amount of gas and ozone concentration, and the quinoline concentration is maintained between 0.7 g/l and 0.9 g./l as a result of the metered addition of aqueous sulfuric acid quinoline solution. The offgas comprised 63 g of $_3/Nm^3$ at the start of the continuous procedure, and 59 g of $O_3/Nm^3$ at the end of the experiment. The ozone consumption was measured and was 230% of theory, calculated on the basis of quinoline, which suggests massive secondary reactions and further reactions of the cleavage products. Finally, PDC began to precipitate out of the solution, which blocked the absorption column.

1 kg of sample was taken in each case from the continuous operation at the start and at the end prior to the precipitation of PDC, and this sample was oxidized as in Example 29 with $H_2O_2$.

The isolated PDC yield was 51.3 g/kg of sample and 5.3 g/kg of sample at the start, corresponding to an isolated total yield of 74%, and at the end 47.2 g/kg of sample and 5.1 g/kg of sample, corresponding to an isolated total yield of 68.5%.

What is claimed is:

1. A process for the preparation of monocarbonyl or biscarbonyl or hydroxyl compounds by ozonization of unsaturated organic carbon compounds which have one or more olefinic or aromatic double bonds which can be cleaved by ozone in the molecule, and subsequent work-up of the ozonization products, which comprises reacting unsaturated organic carbon compounds which have one or more olefinic or aromatic double bonds which can be cleaved by ozone in the molecule,
    a) in an organic solvent or in aqueous solution in 1 to 2 steps continuously in equipment consisting of one to two absorption apparatuses, devices for dissipating heat of the reaction and devices for separating the gas and liquid phase, with countercurrent reactant streams, with ozone in stoichiometric amounts or in excess and
    b) converting the peroxides which form into the corresponding monocarbonyl or biscarbonyl or hydroxyl compounds either by continuous or discontinuous hydrogenation, oxidation or heating, depending on the reaction parameters from step a), where in step a),
    the reactant is fed into the first absorption apparatus at a starting concentration which depends on the reactant used and the reaction conditions, whereas the ozone-bearing $O_2$-stream is introduced into the second absorption apparatus at an ozone concentration which depends on the reactivity of the reactant, such that, in the first absorption apparatus, the reactant used is brought into contact with the ozone stream which is fed into the first absorption apparatus after passing through the second absorption apparatus, as a result of which there is a deficit of ozone in the first absorption apparatus,
    then the reaction mixture, following the reaction of the ozone fed into the first absorption apparatus with the correspondingly introduced reactant, emerges from the first absorption apparatus, is separated into a gas phase and a liquid phase, and the liquid phase, which still comprises unreacted reactant, solvent and the corresponding ozonolysis product, is fed into the second absorption apparatus into which the ozone-bearing $O_2$-stream with the desired starting concentration of ozone is introduced, as a result of which there is an excess of ozone in this apparatus,
    and then, when the reaction is complete, the reaction mixture, after emerging from the second absorption column, is again separated into a gas phase and a liquid phase, and then the liquid phase, which now comprises only the corresponding ozonolysis product in the solvent used, is passed to work-up stage b), and the small percentage of ozone present in the gas phase is optionally introduced into the first absorption apparatus for the further reaction of newly introduced reactant.

2. The process as claimed in claim 1, wherein the amount of ozone is chosen depending on the reactant used such that, for reactive substances, it corresponds to almost stoichiometric ozone consumption up to about 107% of the stoichiometric amount and, for less reactive substances, an ozone consumption of about 107 to 140%, preferably up to 120%, of the stoichiometric amount, based on the reactant.

3. The process as claimed in claim 1, wherein the starting concentration of the reactant is between 1 and 3 mol/l, based on the double bonds, depending on the reactant used and the reaction conditions.

4. The process as claimed in claim 1, wherein reactants which react relatively rapidly relative to the solvent or to the ozonolysis product formed are preferably used.

5. A process as claimed in claim 1, wherein the reactant stream is introduced into the first absorption apparatus and the ozone-bearing $O_2$-stream is also introduced into the first absorption apparatus, some of the stream for the second apparatus being diverted and fed into said apparatus, such that an ozone split is carried out, as a result of which there is again a deficit of ozone in the first absorption apparatus, and then, when the reaction in the first absorption apparatus is complete, the reaction mixture is separated into a gas phase and a liquid phase, the liquid phase, which comprises mainly the corresponding ozonolysis product in the solvent used and residual unreacted reactant, is introduced into the second absorption apparatus, where it is brought into contact with the diverted ozone stream, as result of which there is an excess of ozone in the second absorption apparatus, and then, when the reaction is complete, the reaction mixture is again separated into a gas phase and a liquid phase
    and the liquid phase, which now comprises only the corresponding ozonolysis product in the solvent used, is passed to the work-up phase (step b).

6. The process as claimed in claim 5, wherein the splitting of the ozone-bearing $O_2$-stream takes place in a ratio of first absorption apparatus to second absorption apparatus of 50:50 to 90:10, where the $O_2$-stream fed into absorption apparatus 1 and 2 comprises 4–10% of ozone.

7. The process as claimed in claim 5, wherein the reactant concentration after leaving the first absorption apparatus depends on the splitting ratio of the ozone stream and, in the case of a 90:10 split, is preferably 0.1 mol/l to 0.5 mol/l and, in the case of a 50:50 split, is preferably 0.9 to 2 mol/l.

8. The process as claimed in claim 1, wherein, if the reactants react rapidly relative to the solvent or to the ozonolysis product formed, the ozonolysis is carried out in just one step, in an absorption column.

9. The process as claimed in claim 1, wherein the absorption apparatus used are apparatuses which effect gas-liquid exchange.

10. The process as claimed in claim 9, wherein the absorption apparatuses used are absorption columns, bubble columns, stirred reactors, stirred-tank reactors, mixers or loop reactors.

11. The process as claimed in claim 1, wherein bubble columns are used as absorption apparatuses for the ozonolysis in said aqueous SOLUTION.

12. The process as claimed in claim 11, wherein, the in the case of ozonolysis in the aqueous SOLUTION, bubble columns are used as absorption apparatuses and an ozone split is carried out and wherein the reactant stream is introduced into the first absorption apparatus and the ozone-bearing $O_2$-stream is also introduced into the first absorption apparatus, some of the stream for the second apparatus being diverted and fed into said apparatus, such that an ozone split is carried out, as a result of which there is again a deficit of ozone in the first absorption apparatus, and then, when the reaction in the first absorption apparatus is complete, the reaction mixture is separated into a gas phase and a liquid phase, the liquid phase, which comprises mainly the corresponding ozonolysis product in the solvent used and residual unreacted reactant, is introduced into the second absorption apparatus, where it is brought into contact with the diverted ozone stream, as result of which there is an excess of ozone in the second absorption apparatus, and then, when the reaction is complete, the reaction mixture is again separated into a gas phase and a liquid phase and the liquid phase, which now comprises only the corresponding ozonolysis product in the solvent used, is passed to the work-up phase (step b).

13. The process as claimed in claim 1, wherein the peroxides obtained in step a) are converted into the corresponding monocarbonyl or biscarbonyl or hydroxyl compounds in step b) by continuous or discontinuous hydrogenation, in which the peroxidecontaining ozonolysis product solution obtained from the ozonolysis stage, and a hydrogen stream is introduced into a hydrogenation apparatus which ensures an adequate mass transfer of hydrogen into the liquid phase and which has an initial charge of a solvent and a hydrogenation catalyst, optionally with simultaneous metered addition of a basic additive for regulating the pH, and the volume of the reactor solution is kept constant by level-controlled discharge via the filtration unit, as a result of which the peroxide content of the discharged solution, which is below 0.01 mol/l is continuously controlled.

14. The process as claimed in claim 11, wherein the hydrogenation apparatuses used are stirred-tank reactors, loop reactors, stirred or unstirred bubble columns or fixed-bed reactors.

15. The process as claimed in claim 1, wherein monocarbonyl or biscarbonyl or hydroxyl compounds of the general formula I

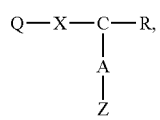

in which

Z is either OH or O and A, when Z is OH, is a single bond and, when Z is O, is a double bond Q is hydrogen or the radicals

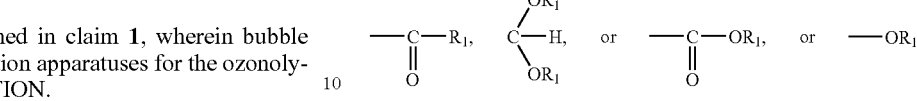

where $R_1$ is H or an ester moiety derived from chiral or nonchiral primary, secondary or tertiary alcohols, X is a straight-chain or branched mono- or divalant, aliphatic alkyl or alkylene radical having 1 to 50 carbon atoms, where this alkyl or alkylene radical may be substituted by one or more groups which are inert under the reaction conditions; an optionally substituted, straight-chain or branched aliphatic alkyl or alkenyl radical having 2 to 50 carbon atoms, where one or more of the —$CH_2$ groups of the alkyl or alkylene chain is replaced by an oxygen atom, a nitrogen atom, a sulfur atom or an —$SO_2$ group; a radical of the formula —$(CH_2)_m$—O—CO—$(CH_2)_p$, where m may be an integer from 1 to 4 and p may be an integer from 1 to 6; a phenyl or phenylene radical, where this phenyl or phenylene radical may be substituted by one or more groups which are inert under the reaction conditions; a mono- or divalent alkylarylene or alkylene-arylene radical having 7 to 50 carbon atoms, where these radicals may be substituted by one or more groups which are inert under the reaction conditions; an optionally substituted heterocycle with one or two heteroatoms in the ring or a single bond between two adjacent carbon atoms, and R is hydrogen, a $C_1$ to $C_{20}$-alkyl radical, —$OR_1$ or the radical

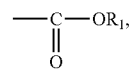

or X and R together form a mono- or bicyclic radical having 4 to 20 carbon atoms which may be mono- or polysubstituted by groups which are inert under the reaction conditions, are prepared.

16. The process as claimed in claim 1, wherein the unsaturated organic carbon compounds which have one or more olefinic or aromatic double bond which can be cleaved by ozone in the molecule used are compounds of the general formula II

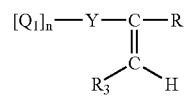

in which n is 0 or 1, $Q_1$ is hydrogen or the radicals

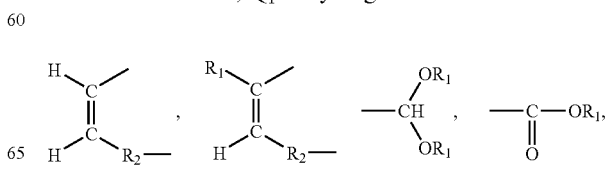

where $R_1$ is as defined in formula I, $R_2$ and $R_3$, independently of one another, are hydrogen, a $C_1$ to $C_4$-alkyl radical, a phenyl or pyridyl radical which is unsubstituted or substituted by groups which are inert under the reaction conditions, or are a —$COOR_1$ radical, or are a radical of the formula $(CH_2)_m$—O—CO—$(CH_2)_p$, where m may be an integer from 1 to 4 and p may be an integer from 1 to 6, or, if n is 1 and $Q_1$ is the radical

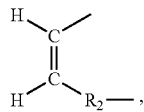

$R_2$ and $R_3$ are together a single bond between two adjacent carbon atoms or are an alkylene radical having 2 to 4 carbon atoms if Y is an o-phenylene radical or an alkylene radical having 2 to 4 carbon atoms and R is a hydrogen atom, otherwise Y has the same meaning as X in formula I, if n is 1, or if n is 0, is either hydrogen or, together with $R_3$ or with $R_3$ and the C=C double bond, is an optionally substituted, aliphatic, araliphatic, aromatic or heteroaromatic radical having 1 to 50 carbon atoms which may be interrupted by oxygen, nitrogen or sulfur, or Y with $R_3$ and the C=C double bond is an optionally substituted mono- or bicyclic radical having 4 to 20 carbon atoms which can contain 1 or 2 heteroatoms from the group S, N or O, or Y and R together form a mono- or bicyclic radical having 4 to 20 carbon atoms which can be mono- or polysubstituted by groups which are inert under the reaction conditions and R is as defined in formula I.

* * * * *